__United States Patent__ [19]

Jones

[11] 4,382,442

[45] May 10, 1983

[54] THORACOSTOMY PUMP-TUBE APPARATUS

[76] Inventor: James W. Jones, 4108 James Dr., Metairie, La. 70003

[21] Appl. No.: 146,504

[22] Filed: May 5, 1980

Related U.S. Application Data

[63] Continuation of Ser. No. 899,547, Apr. 24, 1978, abandoned.

[51] Int. Cl.³ .............................................. A61M 1/00
[52] U.S. Cl. ...................................... 604/28; 604/35; 604/49
[58] Field of Search ................ 128/270, 276, 277, 278, 128/348, 350 R, 350 V; 15/409, 421; 433/91, 95; 119/14.19, 14.2, 14.21

[56] References Cited

U.S. PATENT DOCUMENTS

| | | | |
|---|---|---|---|
| 204,725 | 6/1878 | Gunning | 417/172 |
| 2,804,075 | 8/1957 | Borden | 128/277 |
| 3,101,545 | 8/1963 | Baughan | 433/91 |
| 3,417,009 | 12/1968 | Ericson | 128/276 |
| 3,429,313 | 2/1969 | Romanelli | 128/276 |
| 3,463,159 | 8/1969 | Heimlich | 128/350 V |
| 3,726,283 | 4/1973 | Dye et al. | 128/349 BV |
| 3,732,858 | 5/1973 | Banko | 128/276 |
| 4,062,360 | 12/1977 | Bentley | 128/276 |
| 4,227,533 | 10/1980 | Godfrey | 128/350 V |

OTHER PUBLICATIONS

Chapter 39 Pulmonary Ventilation, Textbook of Medical Physiology, Fourth Edition, A. C. Guyton, M.D., W. B. Saunders Co., Philadelphia, Pa., pp. 456–457.
Foley Catheter Drainage Systems and Bladder Damage, Isaacs, M.D. et al.; Surgery, Gynecology and Obstetrics, May 1971.

*Primary Examiner*—Robert W. Michell
*Assistant Examiner*—J. L. Kruter
*Attorney, Agent, or Firm*—Charles C. Garvey, Jr.

[57] ABSTRACT

A thoracostomy tube provides a pumping arrangement associated with the tube for removing blood and like fluids which enter the tube from the chest cavity area. An elongated tube for conveying liquids is provided, a portion of the tube being insertable, at least in part, into the thoracic cavity area of a patient during a thoracostomy. A valve, which can be, for example, a Heimlich valve, is associated with the tube and is mounted in the distal end portion which is placed into the lung cavity area during the thoracostomy. The valve allows fluids to flow into the tube under the urging of only the pressure normally experienced within the lung cavity. Once fluids pass from the lung cavity area into the tube through the valve, they are removed by a vacuum which is created at the outlet portion of the valve.

16 Claims, 8 Drawing Figures

2

THORACOSTOMY PUMP-TUBE APPARATUS

This is a continuation of application Ser. No. 899,547 filed Apr. 24, 1978, entitled Thoracostomy Pump-Tube Apparatus, now abandoned.

BACKGROUND OF THE INVENTION

1. Field of the Invention

The present invention relates to medical devices, and more particularly to medical devices such as tubes which drain fluids from the human body. Even more particularly, the present invention relates to thoracostomy tubes wherein body fluids such as blood entering the tube structure are quickly removed by a recirculating flow of air creating a vaccum in a portion of the tube and thereby negating the chance for stoppage due to blood clots.

2. General Background and Prior Art

During a thoracostomy, a plastic or like drain tube is attached to the patient in a hole which is formed by the surgeon through the chest wall (see FIG. 7). Thus, fluids accumulating normally in the body after a cardiovascular operation, for example, are collected in the tube in a draining fashion and flow by gravity and by pressure urging from the inner portion of the body to a suitable collection vessel.

The body fluid leaving the lung cavity area through the chest wall can contain a large percentage of blood which can form clots in the tube resulting in stoppage. This presents a problem which requires a nurse or other medical aid to periodically inspect the tube and insure that it is properly flowing.

A pump apparatus to enhance the flow of body fluids through a suitable drain tube during the thoracostomy presents problems. A positive flow of air into the lung cavity would enhance the flow of fluids through the tube much in the same fashion as a sump pump would operate. However, the introduction of a positive pressure into the lung cavity would cause a corresponding increase in pressure within the lungs and a subsequent deflating or even collapse of the lungs themselves which would be undesirable.

To introduce a pure suction into the lung cavity would enhance removal of fluids from the lung cavity area as is desirable, but would cause a decrease in pressure within the lungs, thereby expanding the lungs and causing the muscles to work harder in order to deflate the lungs during exhalation.

3. General Description of the Present Invention

The present invention solves all of these prior art problems and shortcomings in a simple and inexpensive manner. The present invention provides a thoracostomy tube-pump apparatus which is comprised of a drain tube which can be mounted, at least in part, in the chest cavity area of a patient during a thoracostomy. A valve is attached to the distal end portion of the tube which end portion is placed within the lung cavity. The valve is designed to allow fluids to naturally flow under the normal pressure within the lung cavity through the valve into the drain tube. After fluids have passed through the valve structure, a vacuum is provided within the tube by means of a recirculating flow of air which vacuum promptly removes the fluids from the tube as is desirable.

The valve structure provided within the distal end portion of the tube is a Heimlich type valve. The Heimlich valve allows fluids to flow from the chest cavity area through the valve and into the tube through the normal urging of pressure which is normally present within the chest and lung cavity area. Once the fluids have passed through the Heimlich valve structure, a vacuum is provided which can be in the form of a suction attached to the proximal end portion of the tube. At least one recirculation line is mounted on the inner portion of the tube providing an air inlet at the proximal end portion of the tube, the air inlet receiving air from the exterior portion of the tube and routing this air through the center of the tube and discharging it adjacent the valve outlet. Thus, a suction is provided in the form of a vacuum created at the outlet portion of the valve. The valve by its nature provides a check for disallowing the flow of air into the lung cavity which would collapse the lung when a patient is inhaling. During exhalation, and under normal lung cavity pressure, fluids can travel from the lung cavity area to the Heimlich valve and into the tube structure for their prompt removal therefrom.

BRIEF DESCRIPTION OF THE DRAWINGS

For a further understanding of the nature and objects of the present invention, reference should be had to the following detailed description, taken in conjunction with the accompanying drawings, in which like parts are given like reference numerals and wherein.

DETAILED DESCRIPTION OF THE PREFERRED EMBODIMENT

Figure 1:
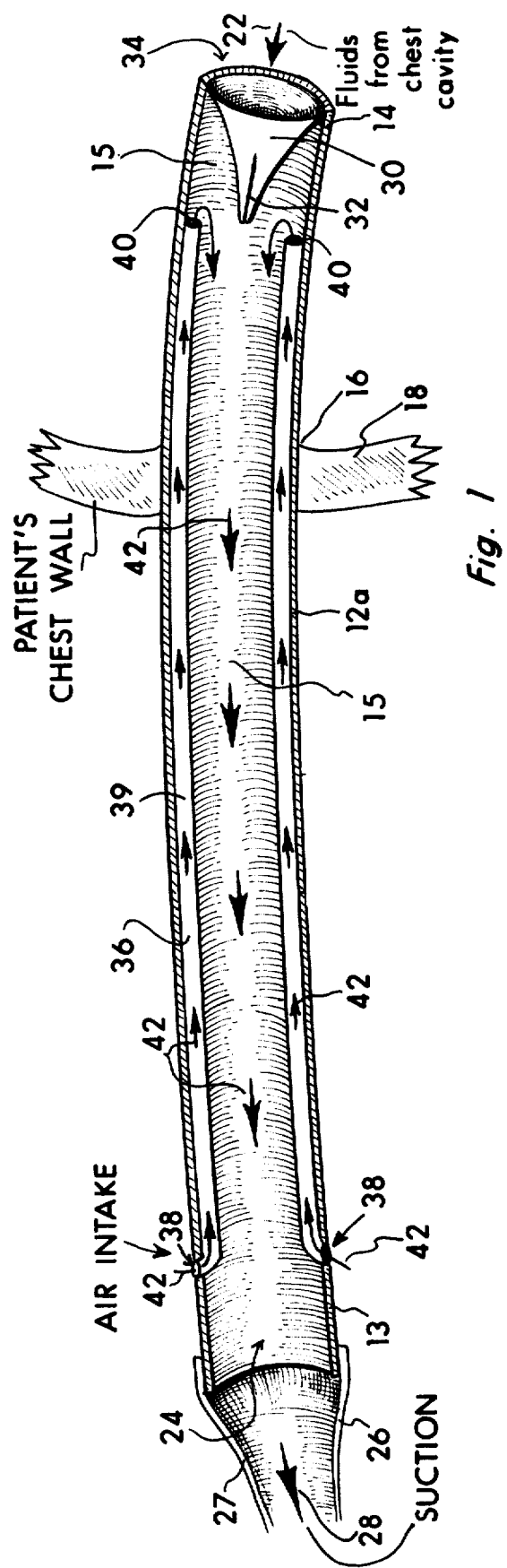
FIG. 1 is a sectional schematic view of the preferred embodiment of the apparatus of the present invention.

FIG. 1 best illustrates the preferred embodiment of the apparatus of the present invention designated generally by the numeral 10 FIG. 1. Thoracostomy tube 10 is comprised generally of a drain tube 12 having a proximal end portion 13 and a distal end portion 14. In FIG. 1, the thoracostomy tube 10 is schematically illustrated during a thoracostomy showing its mounting through an opening 16 formed in the chest wall 18 portion of the patient.

The distal end portion 14 of drain tube 12 is provided with an opening 34 for allowing the flow of body fluids from the chest cavity area into the tube 12 as is desirable. The flow of fluids from the chest cavity area is schematically illustrated by arrow 22 in FIG. 1.

The proximal 13 end portion of the tube 12 provides a proximal end opening 24 to which a suitable vacuum means or suction 26 can be attached. The direction of the flow of air through suction 26 is illustrated schematically by the arrow 28 in FIG. 1. Suction 26 as illustrated in FIG. 1 is merely a suction tube 27 which can be of plastic, rubber or the like, and which can be attached to any suitable vacuum source as is known in the art and as is provided in hospitals, medical offices, and like institutions.

A valve 30 is provided at the distal end portion 14 of drain tube 12 as is best seen in FIG. 1. Valve 30 can be of a Heimlich type. Such a valve 30 allows the flow of fluids in a direction from the distal end portion 14 of tube 12 to the proximal end portion 13 thereof. Such a tube can be in the form of a flexible rubberized tube, with the outlet portion 32 shown in a collapsed closed condition in FIG. 1. The opening 34 of valve 30 would be attached to the walls 12a of tube 12, which tube wall 12a would be manufactured of a slightly resilient or rigid material for sustaining the tube lumen. A suitable stiffened plastic such as polypropylene would suffice as a tube wall 12a. Valve 30 could be a flexible material as is utilized in the construction of penrose type rubber drains.

Figure 4:
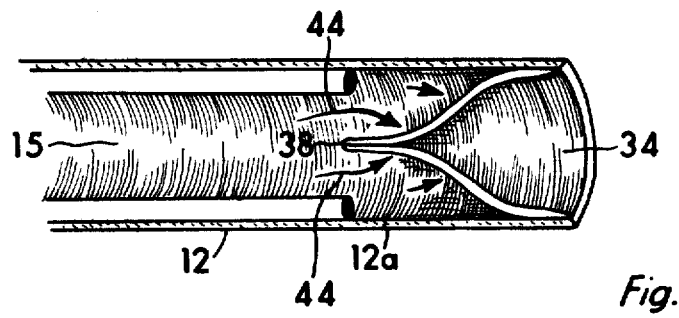
FIG. 4 is a sectional view of the valve portion of the preferred embodiment of the apparatus of the present invention shown in a closed position.
Figure 5:
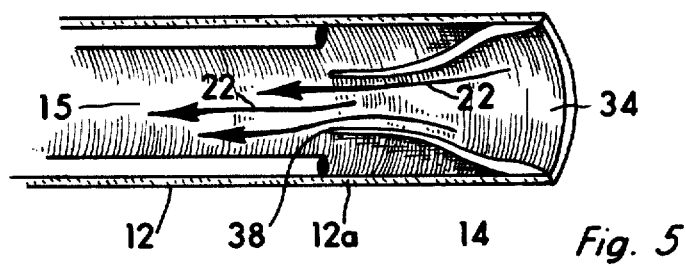
FIG. 5 is a sectional view of the valve portion of the preferred embodiment of the apparatus of the present invention with the valve shown in an open position.

In FIG. 1, opening 34 of valve 30 would be attached circumferentially and sealably to tube wall 12a, thus retaining opening 34 in an open position at all times and preventing leaks around the valve 30 structure. The outlet 32 portion of valve 30 would normally provide the valving portion of the valve 30 and would operate from a closed position as is illustrated in FIGS. 1 and 4 to an open position as is illustrated in FIG. 5. The operation of valve 30 would normally be controlled by pressure, with increased pressure at the outlet portion of 32 of valve 30 causing the valve to close, thereby preventing the inadvertent travel of increased pressurized air into the lung cavity where the lungs themselves could be deflated or collapsed.

Conversely, an increased pressure within the lung cavity area would cause valve 32 to open, allowing fluids such as blood, water, and similar body fluids to flow through the valve 30 and outlet 32 into the inner bore 15 portion of drain tube 12 as is desirable.

A vacuum is produced within tube 12 into bore 15 in that portion of the tube 12 beyond the outlet 32 of valve 30. As can be seen best in FIG. 1, this vacuum is produced by means of a suction 26 which is attached to the proximal 13 end portion of tube 12 and by a recirculating air flow as will be described more fully hereinafter.

A pair of air conveying conduits 36 are provided on the inner bore 15 portion of tube 12. Each hose 36 is provided with an air intake 38 and an air discharge 40. The normal flow of air during operation of tube 10 will be from air intake 38 through the inner bore 39 of conduit 36 to air discharge 40. Air discharged from discharge port 40 will travel from discharge 40 through bore 15 to suction 26 as is illustrated by arrows 42 in FIG. 1. Arrows 42 in FIG. 1 schematically illustrate the flow of air from air intake 38 through the bore 39 of conduit 36 out discharge 40 and through the bore 15 of tube 12 to suction 26. One skilled in the art will note that a vacuum will be produced by such a recirculating flow of air within the bore 15 of tube 12 adjacent the outlet 32 of valve 30 and throughout the bore 15 of tube 12 to suction 28. This vacuum created within tube 12 will promptly remove fluids which migrate (see arrow 22, FIG. 1) from the chest cavity area through the opening 34 at the distal end portion 14 of thoracostomy tube 10. Fluids flowing from the chest cavity area will enter valve 30 through the inlet portion 34 thereof. With the urging of natural pressure created within the chest cavity area, such fluids will pass through the outlet portion 32 of valve 30 and adjacent discharges 40, any such fluids flowing through valve 30 and outlet 32 into bore 15 will promptly be removed by suction 26 as is desirable.

Thus the present invention will solve the problem of clotting seen in prior art thoracostomy tubes.

FIGS. 4 and 5 illustrate more particularly the operation of valve 30 during its closed and open posture respectively. In FIG. 4, valve 30 is shown in a closed position due to increased back pressure within the bore 15 of tube 12. Arrows 44 schematically illustrate the flow of air within the bore 15 of tube 12 due to an increased pressure within tube 12 closing valve 30 as is desirable. In the preferred embodiment, a Heimlich type valve 30 is utilized which provides a flexible rubberized or like pliable end portion at outlet 38 which merely collapses in a closing manner when the presence of an increased pressure occurs.

FIG. 5 illustrates the valve 30 portion of the present invention during normal flow of fluids (see arrows 22, FIG. 5) from the chest cavity area through tube 12. When the normal natural pressure within the lung cavity urges fluids into the proximal end portion 14 of tube 12, the outlet 38 of valve 30 will open allowing the fluids to flow through as is illustrated by arrow 20 in FIG. 5. As aforementioned, the presence of a vacuum at outlet 30 during normal operation of thoracostomy tube 10 causes the fluids to be promptly removed by suction as is desirable.

Figure 6:
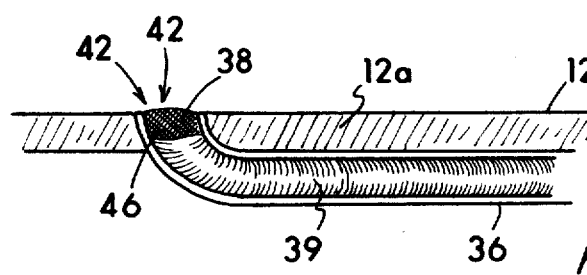
FIG. 6 is a detailed sectional view illustrating the air intake portion of the preferred embodiment of the apparatus of the present invention.
Figure 7:
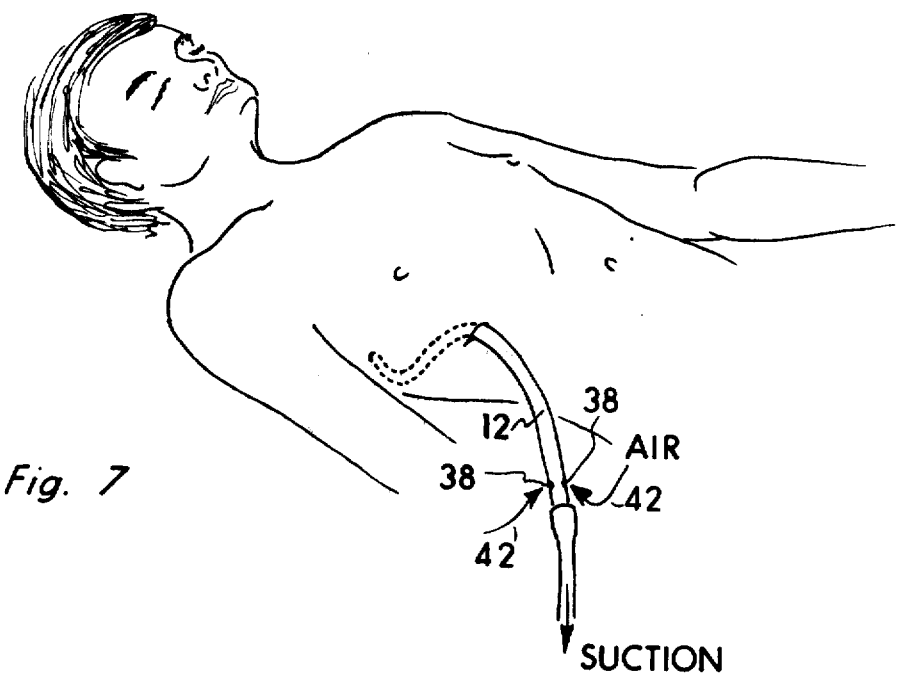
FIG. 7 is a schematic illustration of the preferred embodiment of the apparatus of the present invention shown during its use on a patient during a thoracostomy.
Figure 8:
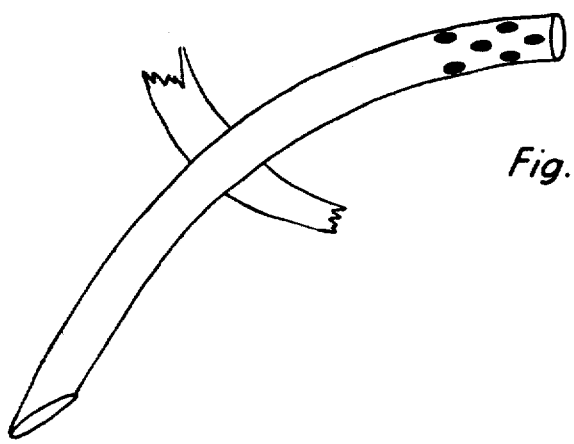
FIG. 8 is a sectional view of a typical prior art type thoracostomy tube.

In FIG. 6, there can be seen a detailed view of the air intake 38 portion of conduit 36 where the bore 39 of conduit 36 outcrops through the tube wall 12A portion of tube 12. The arrows 42 of FIG. 6 indicate the flow of air into conduit 36 through air intake 38. In FIG. 6, there is seen a screen member 46 which covers opening 38. In the preferred embodiment, screen 46 can be of a Millipore type filter which could filter microorganisms thereby removing them from the air stream 42 entering the inner bore 39 of conduit 36 through opening 38. Such a micro biological filter provided opening 38 of conduit 36 would be desirable.

Figure 2:
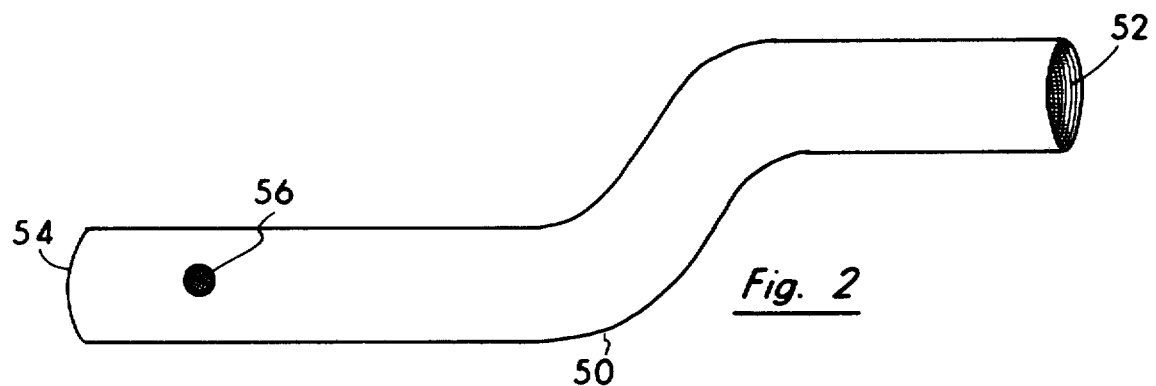
FIG. 2 is a perspective view of an alternative embodiment of the apparatus of the present invention.
Figure 3:
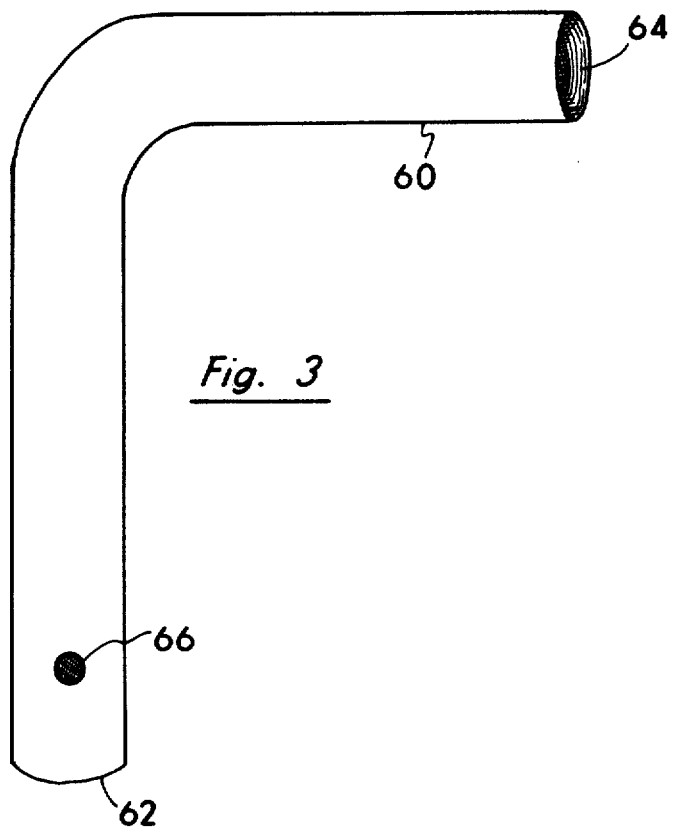
FIG. 3 is a perspective view of a second alternative embodiment of the apparatus of the present invention.

FIGS. 2 and 3 illustrate alternative embodiments of the apparatus of the present invention. In FIG. 2, there can be seen a thoracostomy tube 50 having a curved or S-shaped construction. Note that tube 50 provides a distal 52 end portion and a proximate 54 end portion, with intakes 56 being provided, intakes 56 corresponding to and being analogous with the intakes 38 of tube 10.

In FIG. 3, a "L-shaped" tube 60 is provided having a proximate 62 end portion and a distal 64 end portion thereof. Air intake 66 is further shown in FIG. 3. The embodiment shown in FIGS. 2 and 3 would have identical inner construction with tube 10 as is illustrated in FIG. 1. The S-shaped and L-shaped tubes 50, 60, respectively, are alternative shapes of construction. Such varied shapes provide the surgeon with an availability of varied tube constructions for reaching various portions of the anatomy within the lung cavity where fluids may have accumulated, or may be thought to accumulate. Further, such varied shapes can easily be provided using the construction and teaching of the present invention, thus adapting the present invention to a variety of equivalent tube structures within the teaching of this invention.

What is claimed as invention is:

1. A thoracostomy pump-tube apparatus comprising:
   a. tube means for conveying fluids from the lung cavity area of a patient to an area external therefrom, said tube means having proximal and distal end portions, said distal end portions being normally inserted into the lung cavity area of a patient during a thoracostomy;
   b. valve means placed in the distal end portion of said tube means for allowing the single direction flow of fluids from said lung cavity area into said tube means and past said valve means with said valve means disallowing backflow of fluids from within said tube means back into the patient's chest cavity;
   c. fluid discharge means operative within said tube means for continuously assisting the removal of fluids from said tube means which fluids have entered said tube means through said valve means;
   d. said fluid discharge means positioned adjacent to the valve means and placed within the walls of the tube.

2. The thoracostomy pump-tube apparatus of claim 1, wherein said tube means is a tube having a proximal end portion and a distal end portion, there being further provided a fluid conveying bore in said tube for conveying fluids from said distal end portion to said proximal end portion, and said valve means is affixed to the distal end portion of said tube.

3. The thoracostomy pump-tube apparatus of claim 1, wherein said removing means is comprised in part of a flow of air flowing generally within said tube means from a position at said valve means to the proximate end of said tube means.

4. The thoracostomy pump-tube apparatus of claim 1, wherein said valve means is a valve attached to the distal end portion of said tube means.

5. The thoracostomy pump-tube apparatus of claim 1, wherein said valve means is a heimlich valve.

6. The thoracostomy pump-tube apparatus of claim 1, wherein said removing means is comprised of a source of vacuum attachable to the proximal end portion of said tube, and at least one air recirculation conduit having proximate and distal conduit end portions adjacent respectively the proximate and distal end portion of said tube means and forming therebetween an air conveying conduit bore, with said distal conduit end opening at said valve means and said proximate conduit end opening at said proximate end of said tube but opening through the tube wall to atmosphere at a provided air intake.

7. The thoracostomy pump-tube apparatus of claim 6, wherein there if further provided filtration means on said air intake for removing particles from the air traveling into said hose through said air intake.

8. The thoracostomy pump-tube apparatus of claim 7, wherein said filtration means is a filter capable of filtering microorganisms.

9. A thoracostomy pump-tube apparatus comprising:
   a. an elongated tube having proximate and distal end portions and providing therebetween a continuous bore for conveying fluids from end portion of said tube to the other end portion thereof;
   b. valve means placed in the distal end portion of said tube for valving the flow of fluids from the chest cavity of a patient into the tube bore, said valve means allowing fluid flow from the patient's chest cavity through said valve means into the tube bore responsive to natural pressure created within the chest cavity area, said valve means disallowing backflow from the tube bore into the chest cavity passed said valve means;
   c. at least one elongated conduit positioned within the tube bore of said tube, said conduit having proximate and distal end portions corresponding with the proximate and distal end portions of said tube with the distal end portion of said conduit providing an opening adjacent the discharge side of said valve means and said conduit providing at the proximate end portion of said tube an opening connected with a provided air intake formed in the tube wall;
   d. a source of vacuum connected during operation to the proximate end portion of said tube, said vacuum creating a circulation of air from said air intake through said conduit to the discharge side of said valve and thence to the proximate end portion of said tube, this circulation effecting a removal of fluids entering said tube through said valve means.

10. A post-operative method for removing fluids from the chest cavity of a surgical patient comprising the steps of:
    a. inserting the distal end of an elongated tube partially into the chest cavity of a patient with one end portion of the tube remaining in the chest cavity area;
    b. valving at the distal end of the tube, controlling the flow of fluids from the chest cavity into the tube inner bore with said valving mounted to the distal end portion of the tube;
    c. flushing the tube through a discharge means adjacent the valve;
    d. disallowing backflow of fluids from the tube into the chest cavity; and
    e. removing fluids which have entered the tube bore through the distal end portion thereof as such fluids pass through the valve.

11. The method of claim 10, wherein in step "d" fluids are removed by circulating a flow of air from the distal end portion of the tube downstream from the valve to the proximate end portion of the valve.

12. The method of claim 11, wherein there is provided the additional step of filtering the stream of air.

13. The method of claim 10, wherein in step "a", the tube inserted into the chest cavity provides a Heimlich valve at the distal end portion thereof.

14. The method of claim 10, wherein in step "e" the fluids which pass the valve are continuously removed from the tube.

15. The method of claim 10, wherein in step "e" the fluids which pass the valve are removed automatically from the tube at least periodically.

16. The method of claim 15, wherein in step "e" the fluids are removed from the tube without human intervention.

* * * * *